(12) United States Patent
Navab

(10) Patent No.: US 8,090,174 B2
(45) Date of Patent: Jan. 3, 2012

(54) VIRTUAL PENETRATING MIRROR DEVICE FOR VISUALIZING VIRTUAL OBJECTS IN ANGIOGRAPHIC APPLICATIONS

(76) Inventor: Nassir Navab, München (DE)

( * ) Notice: Subject to any disclaimer, the term of this patent is extended or adjusted under 35 U.S.C. 154(b) by 567 days.

(21) Appl. No.: 12/297,150

(22) PCT Filed: Apr. 11, 2007

(86) PCT No.: PCT/EP2007/003203
§ 371 (c)(1),
(2), (4) Date: Oct. 14, 2008

(87) PCT Pub. No.: WO2007/115824
PCT Pub. Date: Oct. 18, 2007

(65) Prior Publication Data
US 2010/0152570 A1    Jun. 17, 2010

(30) Foreign Application Priority Data
Apr. 12, 2006 (EP) ..................................... 06007723

(51) Int. Cl.
*G06K 9/00* (2006.01)

(52) U.S. Cl. .......... 382/128; 382/154; 600/424; 355/53; 345/32; 345/427; 356/73

(58) Field of Classification Search .................. 600/407, 600/410, 411, 424, 443; 382/128, 154; 345/32, 345/427; 355/53; 356/73
See application file for complete search history.

(56) References Cited

U.S. PATENT DOCUMENTS

| 6,628,977 | B2 | 9/2003 | Graumann et al. |
| 6,711,433 | B1 | 3/2004 | Geiger et al. |
| 6,961,116 | B2 * | 11/2005 | Den Boef et al. ............... 355/53 |

(Continued)

FOREIGN PATENT DOCUMENTS
WO       WO 00/56215       9/2000

(Continued)

OTHER PUBLICATIONS

Ronald T. Azuma, "A Survey of Augmented Reality," Presence, Cambridge, MA, US, Aug. 1997, pp.1-48.

(Continued)

*Primary Examiner* — Tse Chen
*Assistant Examiner* — Baisakhi Roy
(74) *Attorney, Agent, or Firm* — Donald B. Paschburg; F. Chau & Associates, LLC

(57) ABSTRACT

A virtual mirror device for visualizing virtual objects in angiographic applications, having an interactive virtual mirror, a 3D or 4D medical image of a patient's anatomy co-registered with a calibrated 2D X-ray image of the patient's anatomy, and a displaying device provided such that the 2D X-ray image of the patient's anatomy, the co-registered 3D or 4D medical image of the patient's anatomy and the interactive virtual mirror viewed from the viewpoint of the X-ray source of the X-ray imaging system, are presented in a common coordinate system, providing full integration and combined visualization of the reconstruction of 3D or 4D medical image of the patient's anatomy, the 2D X-ray image of the patient's anatomy and the virtual mirror onto the displaying device.

13 Claims, 2 Drawing Sheets

U.S. PATENT DOCUMENTS

| | | | |
|---|---|---|---|
| 7,194,117 B2 * | 3/2007 | Kaufman et al. | 382/128 |
| 7,259,731 B2 * | 8/2007 | Allen et al. | 345/32 |
| 7,319,506 B2 * | 1/2008 | Den Boef et al. | 355/53 |
| 7,375,728 B2 * | 5/2008 | Donath et al. | 345/427 |
| 7,564,534 B2 * | 7/2009 | Den Boef et al. | 355/53 |
| 7,693,325 B2 * | 4/2010 | Pulla et al. | 382/154 |
| 2001/0007919 A1 | 7/2001 | Shahidi | |
| 2004/0091845 A1 * | 5/2004 | Azerad et al. | 434/263 |
| 2004/0254454 A1 * | 12/2004 | Kockro | 600/424 |
| 2005/0272991 A1 | 12/2005 | Xu et al. | |
| 2008/0074648 A1 * | 3/2008 | Lampalzer | 356/73 |

FOREIGN PATENT DOCUMENTS

| | | |
|---|---|---|
| WO | WO 02/100284 | 12/2002 |
| WO | WO 2007/115824 | 10/2007 |
| WO | WO 2007/115826 | 10/2007 |

OTHER PUBLICATIONS

International Search Report for PCT/EP2007/003205.
International Search Report for PCT/EP2007/003203.
International Search Report for PCT/EP2007/003206.

* cited by examiner

VIRTUAL PENETRATING MIRROR DEVICE FOR VISUALIZING VIRTUAL OBJECTS IN ANGIOGRAPHIC APPLICATIONS

CROSS-REFERENCE TO RELATED APPLICATIONS

This application is a national stage entry of International Application No. PCT/EP2007/003203 filed on Apr. 11, 2007, the content of which is herein incorporated by reference in its entirety.

BACKGROUND

1. Technical Field

The present invention relates to a method and to a virtual penetrating mirror device for visualizing virtual objects in angiographic applications from arbitrary view points with substantial use in medical applications.

2. Discussion of Related Art

A major roadblock for simultaneous visualisation of 2D and 3D data in many medical applications is the fact that the user cannot take full advantage of the 3D virtual data. This usually requires the user to move the virtual object, which disturbs the real/virtual alignment.

The prior art related to the present invention is disclosed for example in EP06007724.5 and in EP06009222.8.

EP06007724.5 relates to a method and to a virtual penetrating mirror device for visualizing virtual objects from arbitrary view points within an augmented reality environment, with substantial use in medical and industrial applications.

EP06009222.8 relates to a method and to a device, which is a registration-free augmentation device, for collocating the view of a tracked endocope with an intraoperative reconstruction of anatomy for image guided surgery using an endoscope and a C-arm or another imaging device capable of intraoperative 3D or 4D reconstructions of anatomy with one or more co-registered tracking systems to localize the endoscope, the imaging device and its reconstructions, as well as additional surgical instruments in a common coordinate system.

However neither EP06007724.5 nor EP06009222.8 discloses any concrete use of the mentioned devices and methods for particular medical applications. In addition, both EP06007724.5 and EP06009222.8 integrate the virtual mirror into the real views of the surgery captured by optical cameras, but none of them integrates the virtual mirror into the projection geometry of an X-ray imaging system.

Angiographic imaging is a widely used technique for intravascular interventions. In such treatments a preoperative 3D data set is usually acquired for diagnosis and planning. This data set can be visualized using state-of-the-art volume rendering techniques and shows detailed information of the patient's anatomy. 3D data sets are commonly acquired using CTA (computed tomography). During the intervention an intraoperative imaging device captures the current state of anatomy of the patient and for instance a placed catheter for navigation. In clinical practice, 2D fluoroscopic projections of the region of interest are acquired lacking spatial resolution and detailed tissue information compared to the visualized, preoperative data sets. Registration of pre- and intraoperative data sets allows physicians to view the 3D data together with 2D angiographic and/or fluoroscopic data.

Much attention has been drawn to the problem of 2D-3D registration of angiographic images. Intensity-based methods register two data sets by creating artificial X-ray projections (Digitally Reconstructed Radiographs, DRR) and optimizing cost functions directly evaluating pixel intensities. Since vessel structures are the dominant features in angiographic images, they are often exclusively used for feature-based registration. Research is focusing on determination of corresponding points on vessel structures, choice of suitable metrics with (near) projective invariance, and derivation of globally converging optimization procedures. Hybrid approaches register segmentations of the (reconstructed) vasculature using intensity-based methods. All of these works address the problem of registration, however, when the registered 2D-3D data is presented, the user still observes a 2D projective view of this registration. This limits the ability of the user to take advantage of the 3D information.

Therefore, a need exists for taking full advantage of the 3D information, when the registered 2D-3D data is presented and the user still has to observe a 2D projective view of this registration.

BRIEF SUMMARY

A virtual penetrating mirror device visualizes virtual objects within the registered 2D-3D angiographic scene.

A method for interactive visualization of the registered 3D data from new perspectives includes viewing a virtual mirror from the same viewpoint as the X-ray source of the co-registered 2D X-ray image.

BRIEF DESCRIPTION OF THE DRAWINGS

The invention will now be elucidated by reference to the embodiment partially illustrated schematically in the drawings regarding an exemplary medical application scenario.

DETAILED DESCRIPTION OF PREFERRED EMBODIMENTS

Figure 1:
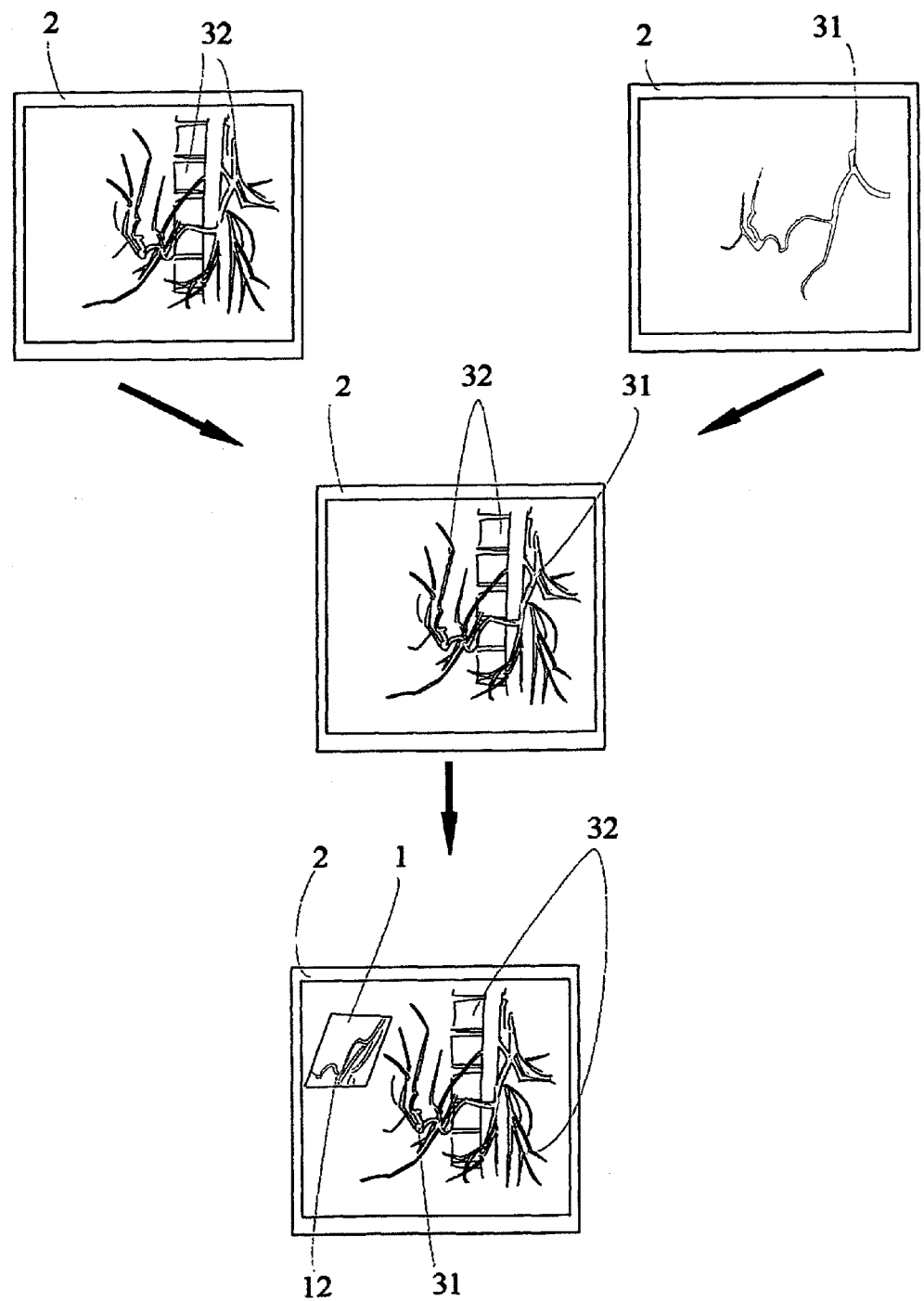
FIG. 1: a schematic overview of the virtual penetrating mirror device for visualizing virtual objects in angiographic application into the 2D3D registered visualization.

A virtual penetrating mirror device visualizes virtual objects within the registered 2D-3D angiographic scene.

A method for interactive visualization of the registered 3D data from new perspectives includes viewing a virtual mirror from the same viewpoint as the X-ray source of the co-registered 2D X-ray image.

Due to the Virtual penetrating mirror device for visualizing virtual objects in angiographic applications the 3D part of the visualization can be intuitively perceived and additional information about the 3D structure can be explored interactively. The virtual mirror can be positioned into the scene and fits into the viewing projective geometry of the angiography imaging system. A user interface allows the user to move the virtual mirror, which in turns reflects the registered 3D angiographic data. This allows the visualization of the complex 3D anatomical structures including the 3D vessels without disturbing the alignment of 2D angiography with the 3D data. The user can also change the size of the virtual mirror and move it forward and or backward in regard to the viewing geometry of the angiographic system. Therefore, a new method is introduced for visualizing registered 2D and 3D angiography data. The 3D data can be obtained from Computer Tomography Angiography, MRI, 3D Ultrasound imaging or any other source of imaging.

The 2D image is an angiographic or fluoroscopic image.

Once the two sets of the 2D and 3D data are aligned, in order to visualize and analyze the registered 3D data, a virtual mirror is positioned in 3D space.

The virtual mirror is acting as a mirror relative to the projection geometry of the X-ray imaging system. By moving this virtual mirror the user can analyze the 3D shape of patient anatomy for instance the blood vessels while keeping the alignment of the 3D and 2D data intact. This user interface consists of an interactive virtual mirror positioned within the aligned 3D data, which reflects the structures of the segmented or not segmented 3D data by surface or volume rendering and through the reflection onto the angiographic virtual mirror.

The said virtual angiographic mirror is controlled interactively by the user who can move the virtual mirror, rotate it and position it and change its size or all combinations of such actions.

The said interaction can for instance be done using a regular mouse interaction or by tracking a hand-held device, which is virtually connected to the virtual angiographic mirror allowing the user to position it naturally into the virtual space.

The invention allows the user to observe and visualize the 3D patient data while keeping its alignment with 2D angiographic or fluoroscopic image undisturbed.

The said invention could be modified such that the mirror visualizes a Digitally Reconstructed Radiograph (DRR), Maximum Intensity Projection (MIP) or any other imaging technique. The 2D angiographic image could consist of a subtracted angiographic image. Such image is obtained by subtraction of patient's X-ray image after contract injection and the one before such injection, resulting in a high contrast image showing almost only the contrasted blood vessels.

FIG. 1 shows the components of the visualization on a displaying device 2 consisting of the medical imaging data 3 and the virtual mirror 1. Combination of the 2D X-ray angiography image of patient's anatomy 31, which can be a subtracted X-ray angiography image, with the 3D or 4D medical image of patient's anatomy 32, which can be a maximum intensity projection, results in the registered 2D X-ray angiography image of patient's anatomy with 3D or 4D medical image of patient's anatomy 33, which provides for instance the view from the view point of an x-ray source onto visualized medical imaging data 3. Integration of the mirror into the visualization provides additional perspectives onto due to the 3D or 4D medical image of patient's anatomy 32 showing an image of the reflected 3D or 4D medical image of patient's anatomy by virtual mirror on displaying device 12.

Figure 2:
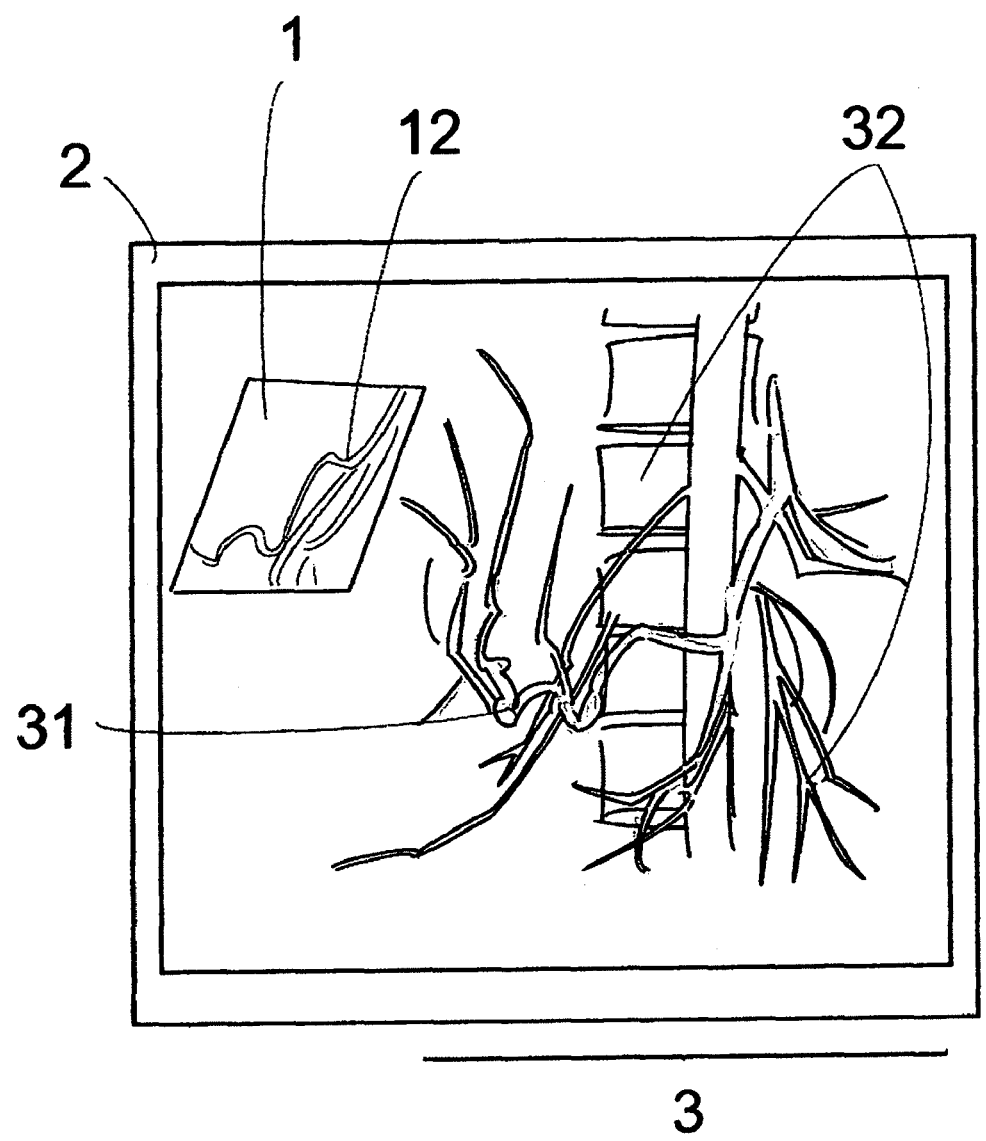
FIG. 2: a schematic view of a visualization of exemplary virtual objects including the virtual mirror.

FIG. 2 shows the 3D or 4D medical image of patient's anatomy 32 including the virtual mirror 1 on the displaying device 2.

The virtual mirror provides an image of the reflected 3D or 4D medical image of patient's anatomy by virtual mirror on displaying device 12.

REFERENCE LIST OF DRAWINGS

1 virtual mirror
12 image of the reflected 3D or 4D medical image of patient's anatomy by virtual mirror on
2 displaying device
3 registered 2D X-ray angiography image of patient's anatomy with 3D or 4D medical image of patient's anatomy
31 2D X-ray image of patient's anatomy
32 3D or 4D medical image of patient's anatomy

The invention claimed is:

1. A device for visualizing virtual objects in angiographic applications adapted to display a 3D or 4D medical image and a corresponding calibrated 2D X-ray image on a displaying device, wherein the 3D or 4D medical image is co-registered with the calibrated 2D X-ray image, wherein the device is adapted to display the 2D X-ray image, the co-registered 3D or 4D medical image and an in e active virtual mirror viewed from the viewpoint of the X-ray source of the X-ray imaging system in a common coordinate system, and the device is further adapted to provide on the displaying device full integration and combined visualization of the 3D or 4D medical image, the 2D X-ray image and the virtual mirror, which reflects the 3D or 4D medical image.

2. The device according to claim 1, characterized in that the 2D X-ray image is a subtracted X-ray angiography image.

3. The device according to any one of the preceding claims, characterized in that the virtual mirror visualizes digitally reconstructed radiographs generated from the 3D or 4D medical image.

4. The device according to any one of the preceding claims, characterized in that the virtual mirror visualizes a maximum intensity projection generated from the 3D or 4D medical image.

5. The device according to any one of the preceding claims, characterized in that the 3D or 4D medical image is obtained by an Ultrasound Imaging Device.

6. The device according to any one of the preceding claims, characterized in that the 3D or 4D medical image is obtained by a Magnetic Resonance Imaging system.

7. The device according to any one of the preceding claims, characterized in that the 3D or 4D medical image is obtained by a Computer Tomography imaging system.

8. The device according to any one of the preceding claims, characterized in that the 3D or 4D medical image of is obtained by a mobile or stationary X-ray C-arm.

9. The device according to any one of the preceding claims, characterized in that the position, orientation, size, scaling and color of the angiographic virtual mirror is controllable interactively.

10. A computer implemented method for visualizing virtual objects in angiographic applications comprising:
    acquiring image data corresponding to a scene, wherein first image data of the scene includes two dimensions and second image data of the scene includes at least three dimensions;
    determining calibrated first image data using the first image data;
    co-registering the calibrated first image data and the second image data; and
    displaying co-registered calibrated first image data and second image data and a virtual mirror, wherein the interactive virtual mirror reflects the second image data.

11. The computer implemented method of claim 10, wherein the virtual mirror reflects second image data relative to a projection geometry of the first image data.

12. The computer implemented method of claim 10, further comprising receiving an input adapted to position the virtual mirror for viewing different portions of the second image data without changing a view of the first image data.

13. The computer implemented method of claim 10, further comprising receiving an input adapted to position the virtual mirror for viewing different portions of the second image data without changing an alignment of the co-registered calibrated first image data and second image data.

* * * * *